(12) United States Patent
Bikfalvi et al.

(10) Patent No.: US 8,940,702 B2
(45) Date of Patent: Jan. 27, 2015

(54) MUTANTS PF4 POLYPEPTIDES EXHIBITING AN INCREASED ANTI-ANGIOGENIC ACTIVITY

(75) Inventors: Andreas Bikfalvi, Talence (FR); Herve Prats, Toulouse Cedex (FR); Cathy Quemener, Talence (FR); Alexandre Dubrac, Toulouse Cedex (FR)

(73) Assignees: Institut National de la Sante et de la Recherche Medicale (INSERM), Paris (FR); Universite de Bordeaux, Bordeaux (FR)

( * ) Notice: Subject to any disclaimer, the term of this patent is extended or adjusted under 35 U.S.C. 154(b) by 11 days.

(21) Appl. No.: 13/386,696

(22) PCT Filed: Jul. 26, 2010

(86) PCT No.: PCT/EP2010/060818
§ 371 (c)(1), (2), (4) Date: Feb. 29, 2012

(87) PCT Pub. No.: WO2011/012585
PCT Pub. Date: Feb. 3, 2011

(65) Prior Publication Data
US 2012/0157384 A1 Jun. 21, 2012

(30) Foreign Application Priority Data
Jul. 29, 2009 (EP) .................. 09305712

(51) Int. Cl.
*A61K 38/00* (2006.01)
*A61P 9/10* (2006.01)
*C07K 14/52* (2006.01)

(52) U.S. Cl.
CPC .............. *C07K 14/522* (2013.01); *A61K 38/00* (2013.01)

USPC .......................................... 514/20.8

(58) Field of Classification Search
CPC .............................. A61K 38/00; C07K 14/522
See application file for complete search history.

(56) References Cited

U.S. PATENT DOCUMENTS 7,820,619 B1 * 10/2010 Yeaman et al. ............... 514/2.3

FOREIGN PATENT DOCUMENTS

WO 2006029487 3/2006

OTHER PUBLICATIONS

Maione et al; "Inhibition of Tumor Growth in Mice by an Analogue of Platelet Factor 4 That Lacks Affinity for Heparin and Retains Potent Angiostatic Activity"; Cancer Research, vol. 51, Apr. 15, 1991; pp. 2077-2083.
Eisman et al.; "Structural and Functional Comparison of the Genes for Human Platelet Factor 4 and PF4alt"; Blood, vol. 76, No. 2, Jul. 15, 1990; pp. 336-344.
Hagedorn et al.; "A Short Peptide Domain of Platelet Factor 4 Blocks Angiogenic Key Events Induced by FGF-2"; The FASEB Journal: Official Publication of the Federation of American Societies for Experimental Biology, vol. 15, No. 3, Mar. 2001; pp. 550-552.
Andreas Bikfalvi; "Platelet Factor 4: An Inhibitor of Angiogenesis"; Seminars in Thrombosis and Hemostasis, vol. 30, No. 3, 2004, pp. 379-385.

* cited by examiner

*Primary Examiner* — Thomas S Heard
(74) *Attorney, Agent, or Firm* — Whitham, Curtis, Christofferson & Cook, PC (57) ABSTRACT

The present invention pertains to PF4 muteins which comprise a substitution at position 67, e.g. a L67H substitution, compared to the sequence of the wild-type PF4 protein. Such PF4 muteins exhibit an increased anti-angiogenie activity and a reduced affinity for proteoglycans compared to the wild-type PF4 protein.

15 Claims, 3 Drawing Sheets

MUTANTS PF4 POLYPEPTIDES EXHIBITING AN INCREASED ANTI-ANGIOGENIC ACTIVITY

CROSS-REFERENCE TO RELATED APPLICATIONS

This application is a 371 of International Application Number PCT/EP2010/060818 filed Jul. 26, 2010, and which is incorporated herein by reference.

The present invention pertains to PF4 muteins which comprise a substitution at position 67, e.g. a L67H substitution, compared to the sequence of the wild-type PF4 protein. Such PF4 muteins exhibit an increased anti-angiogenic activity and a reduced affinity for proteoglycans compared to the wild-type PF4 protein.

Angiogenesis, i.e. the development of new blood vessels, is a complex biological process which occurs both in physiological conditions (e.g. during embryonic development, wound healing, etc.) and in pathological conditions (e.g. cancer) (see e.g. Bikfalvi and Bicknell, 2002 Trends Pharmacol Sci. 23:576-82). Angiogenesis is controlled by the net balance between pro-angiogenic and anti-angiogenic factors. Known factors for promoting angiogenesis include the family of fibroblast growth factors, the Vascular Endothelial Growth Factor (VEGF), Platelet-Derived Growth Factor (PDGF) and the angiopoietins.

Molecules capable of inhibiting angiogenesis have been the focus of many anti-cancer research projects since it is believed that tumors need to be vascularized in order to grow, and that diffusible molecules regulate this process (see, e.g., Auguste et al. 2005 Crit. Rev Oncol Hematol. 54:53-61). Anti-angiogenic molecules include antibodies such as avastatin, small chemical molecules, and endogenous factors among which Platelet Factor 4 (PF4).

For the time being, inhibition of angiogenesis in cancer or ocular diseases is mainly based on inhibiting primarily Vascular Endothelial Growth factor (VEGF). Clinical trial and current use of VEGF antagonists in the clinic have demonstrated a number of side effects and resistance to therapy. There is thus a need for obtaining novel anti-angiogenic molecules with improved properties.

The CXC-chemokine family consists of pro-inflammatory cytokines, primarily involved in chemoattraction and activation of specific leukocytes in various immuno-inflammatory responses. The CXC chemokine family is unique because it comprises both angiogenic and angiostatic chemokines. The Platelet Factor 4 (PF4 or CXCL4) was the first chemokine described as a regulator of angiogenesis (Maione et al. 1990 Science. 247:77-9, and WO 85/04397).

Maione et al. (1991 Cancer Res. 51:2077-83) describe the PF4-241 mutant of PF4. This mutant comprises four substitutions compared to the wild-type PF4 protein, namely the K61Q, the K62E, the K65Q and the K66E mutations. The activity of this mutant is independent of heparin binding, and it may thus exhibit reduced toxicity and an improved bioavailability. However, its anti-angiogenic activity is comparable to the anti-angiogenic activity of the wild-type PF4 protein.

WO 2006/029487 discloses a naturally-occurring variant of the PF4, referred to as PF4var1. This variant comprises three substitutions compared to the wild-type PF4 protein, namely the P58L, the K66E and the L67H mutations. The PF4var1 variant has an increased anti-angiogenic activity compared to the anti-angiogenic activity of the wild-type PF4 protein. WO 2006/029487 suggests that the presence of the three P58L, K66E and L67H mutations is crucial for improved anti-angiogenic activity of the PF4var1 variant.

There is a need for obtaining mutants of PF4 having both an increased anti-angiogenic activity and a reduced affinity for proteoglycans.

DETAILED DESCRIPTION OF THE INVENTION

It has surprisingly been found that the L67H mutation is sufficient for conferring both an increased anti-angiogenic activity and a reduced affinity for proteoglycans compared to the wild-type PF4 protein.

More specifically, the inventors have obtained PF4 muteins where, compared to the sequence of the wild-type PF4 protein, one to five amino acids are mutated within the C-terminal sequence. It has been found that all muteins comprising the L67H mutation (alone or in combination with other mutations) exhibit a very substantial increase in anti-angiogenic activity in vitro. This increase in anti-angiogenic activity is accompanied by a reduction in binding affinity to proteoglycans, which contributes to efficient delivery of the PF4 muteins to angiogenic blood vessels.

PF4 Muteins According to the Invention and Fragments Thereof

The invention thus pertains to a polypeptide exhibiting anti-angiogenic activity and comprising a sequence at least 80, 85, 90, 95, 96, 97 or 98% identical to SEQ ID NO: 2, wherein said polypeptide comprises a substitution at position 67 of SEQ ID NO: 2, and wherein said polypeptide:
 i. comprises a sequence identical to amino acids 60 to 67 or 58 to 67 of SEQ ID NO: 4, 5 or 6; and/or
 ii. does not comprise both a lysine to glutamic acid substitution at position 66 of SEQ ID NO: 2 and a leucine to histidine at position 67 of SEQ ID NO: 2.

Such polypeptides are derivable from the wild-type PF4 polypeptide of SEQ ID NO: 2 by one, two, three, four, five, six, seven, eight, nine, ten, eleven, twelve, thirteen or fourteen single point mutations.

Said sequence identical amino acids 58 to 67 of any one of SEQ ID NOs: 4, 5 or 6 is preferably located at the positions of the polypeptide that correspond to amino acids 58 to 67 of SEQ ID NO: 2. For example, said sequence is located at positions 58 to 67 of the polypeptide according to the invention if said polypeptide does not comprise any deletion or insertion compared to SEQ ID NO: 2, but located at positions 57 to 66 of the polypeptide according to the invention if said polypeptide comprises e.g. a deletion at position 1 of SEQ ID NO: 2.

By "anti-angiogenic activity" is meant the capacity to inhibit, partially or totally, the growth of blood vessels. Methods for determining whether a compound exhibits an anti-angiogenic activity are well-known in the art and include, e.g. the assay using bovine aortic endothelial (BAE) cells that is described in example 1. In this assay, BAE cells are stimulated with recombinant FGF2 and cell viability/proliferation is measured.

The invention also pertains to a polypeptide comprising a sequence at least 80, 85, 90, 95, 96, 97 or 98% identical to SEQ ID NO: 2, wherein said polypeptide comprises a substitution at position 67 of SEQ ID NO: 2 (e.g. L67H), and wherein said polypeptide comprises at most two single point mutations within the region extending from position 58 to position 67 of SEQ ID NO: 2 (e.g. K66E and L67H).

The above polypeptides are further referred to as "PF4 muteins according to the invention".

By "PF4" is meant the platelet factor 4, also known under the names of C-X-C motif chemokine 4, oncostatin-A and iroplact. The sequence of the wild-type PF4 protein is shown as SEQ ID NO: 1 (full-length protein) and SEQ ID NO: 2

(mature protein). The sequence of the PF4-241 mutant (mature protein) is shown as SEQ ID NO: 3.

The PF4 muteins according to the invention all comprise a substitution at position 67 of SEQ ID NO: 2. The leucine at position 67 of SEQ ID NO: 2 is preferably replaced with an amino acid having physico-chemical properties that are similar to those of histidine, e.g. with an amino acid with basic side chain selected from the group consisting of histidine, lysine and arginine. Therefore, the leucine at position 67 is preferably substituted with an amino acid with basic side chain. Most preferably, said substitution is a leucine to histidine substitution at position 67 of SEQ ID NO: 2.

The PF4 muteins according to the invention may further comprise other single point mutations, which may be substitutions, insertions or deletions of one amino acid. The other single point mutations are preferably substitutions, which may be conservative or not. The other single point mutations may either correspond to allelic variations of the wild-type PF4 protein of SEQ ID NO: 2, or to non-naturally occurring mutations.

By "conservative substitution" is meant one of the substitutions shown in the table below.

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

Methods for comparing the identity and homology of two or more sequences are well known in the art. The <<needle>> program, which uses the Needleman-Wunsch global alignment algorithm to find the optimum alignment (including gaps) of two sequences when considering their entire length, may for example be used to determine the percentage of identity. The needle program is for example available on the ebi.ac.uk world wide web site.

In a preferred embodiment, the PF4 mutein according to the invention differs from the sequence of SEQ ID NO: 2 (wild-type PF4 protein) or SEQ ID NO: 3 (PF4-241) by the presence of one single amino acid substitution, namely the substitution at position 67 of SEQ ID NO: 2 (e.g. a leucine to histidine substitution). Examples of such PF4 muteins according to the invention include the polypeptides comprising or consisting of SEQ ID NO: 4 or 6. As apparent to the skilled in the art, this embodiment intends to cover a PF4 mutein differing from the sequence of SEQ ID NO: 2 (wild-type PF4 protein) or of SEQ ID NO: 3 (PF4-241 protein) only by the presence of one single amino acid substitution.

In another preferred embodiment, the PF4 mutein according to the invention differs from the sequence of SEQ ID NO: 2 or 3 by the presence of further single amino acid substitutions, i.e. a substitution at position 67 of SEQ ID NO: 2 (e.g. a leucine to histidine substitution) and at least one further single amino acid substitution.

The further single amino acid substitution may for example be selected from the group consisting of:
i. a substitution at position 56 of SEQ ID NO: 2, e.g. a substitution for an amino acid with basic side chain, preferably a glutamine to arginine substitution; and/or
ii. a substitution at position 58 of SEQ ID NO: 2, e.g. a proline to leucine substitution; and/or
iii. a substitution at position 61 of SEQ ID NO: 2, e.g. a lysine to glutamine substitution; and/or
iv. a substitution at position 62 of SEQ ID NO: 2, e.g. a lysine to glutamic acid substitution; and/or
v. a substitution at position 65 of SEQ ID NO: 2, e.g. a lysine to glutamine substitution; and/or
vi. a substitution at position 66 of SEQ ID NO: 2, e.g. a lysine to glutamic acid substitution.

In addition to the substitution at position 67, the PF4 muteins according to the invention may comprise any combination of the above further single amino acid substitutions, e.g. i+ii, i+iii, i+iv, i+v, i+vi, ii+iii, ii+iv, ii+v, ii+vi, iii+iv, iii+v, iii+vi, iv+v, iv+vi, v+vi, i+ii+iii, i+ii+iv, i+ii+v, i+ii+vi, ii+iii+iv, ii+iii+v, ii+iii+vi, iii+iv+v, iii+iv+vi, iv+v+vi, i+ii+iii+iv, i+ii+iii+v, i+ii+iii+vi, ii+iii+iv+v, ii+iii+iv+vi, iii+iv+v+vi, i+ii+iii+iv+v, i+ii+iii+iv+vi, ii+iii+iv+v+vi or i+ii+iii+iv+v+vi. When the further single amino acid substitutions include a glutamic acid substitution at position 66 of SEQ ID NO: 2, the substitution at position 67 is preferably not a leucine to histidine substitution.

In still another preferred embodiment, the PF4 mutein according to the invention differs from the sequence of SEQ ID NO: 2 (wild-type PF4 protein) or of SEQ ID NO: 3 (PF4-241 protein) by the presence of two single amino acid substitutions. Examples of PF4 muteins according to the invention differing from the sequence of SEQ ID NO: 2 or 3 by the presence of two amino acid substitutions include the polypeptides comprising or consisting of SEQ ID NOs: 5, 7 or 8. As apparent to the skilled in the art, this embodiment intends to cover a PF4 mutein differing from the sequence of SEQ ID NO: 2 (wild-type PF4 protein) or of SEQ ID NO: 3 (PF4-241 protein) only by the presence of two single amino acid substitutions.

The PF4 muteins according to the invention may further comprise sequences in addition to the sequence that is at least 80% identical to SEQ ID NO: 2. For example, the PF4 muteins according to the invention may comprise a signal peptide. The signal peptide may be the native signal peptide of PF4 (i.e. amino acids 1 to 31 of SEQ ID NO: 1) or a heterologous signal peptide, e.g. a signal peptide suitable for expression in a given host cell. Alternatively or additionally, the PF4 muteins according to the invention may comprise a linker sequence suitable for linking the mutein to a molecule such as a detectable marker or a cytotoxic agent.

The invention also pertains to polypeptides comprising or consisting of fragments of at least 6 consecutive amino acids of the PF4 muteins according to the invention and exhibiting an anti-angiogenic activity. The fragments preferably include positions 66 and 67 of SEQ ID NO: 2. Most preferably, the fragments include positions 60 to 67 or 58 to 67 of SEQ ID NO: 2.

As used herein, "a fragment that includes positions 58 to 67 of SEQ ID NO: 2", or a "fragment that includes positions 66 and 67 of SEQ ID NO: 2", refers to a conservative fragment of a PF4 mutein according to the invention, wherein said fragment comprises the region of PF4 including these amino acid positions. These fragments comprise at least one single point substitution (i.e. the leucine to histidine substitution at position 67 of SEQ ID NO 2) compared to the corresponding fragment of the wild-type PF4 protein of SEQ ID NO: 2.

Such fragments may comprise or consist of at least 6, 10, 15, 20, 25, 30, 35, 40, 45, 50, 55, 60 or 65 consecutive amino acids of a PF4 mutein according to the invention.

In a specific embodiment, such fragments comprise or consist of at least 6, 10, 15, 20, 25, 30, 35, 40, 45, 50, 55, 60 or 65 consecutive amino acids of any one of SEQ ID NOs: 4, 5, 6, 7 or 8.

In another specific embodiment, such fragments comprise a sequence identical to amino acids 60 to 67 or 58 to 67 of SEQ ID NO: 4, 5 or 6.

The fragment may for example correspond to the short isoform of PF4, which consists of a fragment extending from position 17 to position 70 of SEQ ID NO: 2.

The fragment may also correspond to a peptide, i.e. a polypeptide of less than 50 amino acids.

Such peptides according to the invention may for example be derived from the peptides described in Ragona et al. (2009 Biochem Biophys Res Commun. 382:26-9), Benny et al. (2005 Clin Cancer Res. 11:768-76), Bikfalvi (2004 Semin Thromb Hemost. 30:379-85), Giussani et al. (2003 Cancer Res. 63:2499-505), Hagedorn et al. (2002 Cancer Res. 62:6884-90), Hagedorn et al. (2001 FASEB J. 15:550-2) or Jouan et al. (1999 Blood. 94:984-93) by introducing at least a substitution at position 67 of SEQ ID NO: 2 (e.g. a leucine to histidine substitution).

The peptides according to the invention may also be derived from one of the peptides described in WO 02/06300. They may for example comprise or consist of the fragment extending from position 47 to position 70 of SEQ ID NO: 2. In a preferred embodiment, the peptide comprises or consist of the fragment extending from position 17 to position 34 of SEQ ID NO: 2 fused in frame with the fragment extending from position 47 to position 70 of SEQ ID NO: 2. The peptide of SEQ ID NO: 9 is an example of such a peptide according to the invention.

The peptides of the invention may optionally comprise chemical modifications improving their stability and/or their biodisponibility. Such chemical modifications aim at obtaining peptides with increased protection of the peptides against enzymatic degradation in vivo, and/or increased capacity to cross membrane barriers, thus increasing its half-life and maintaining or improving its biological activity. Any chemical modification known in the art can be employed according to the present invention. Such chemical modifications include but are not limited to:

- modifications to the N-terminal and/or C-terminal ends of the peptides such as e.g. N-terminal acylation (preferably acetylation) or desamination, or modification of the C-terminal carboxyl group into an amide or an alcohol group;
- modifications at the amide bond between two amino acids: acylation (preferably acetylation) or alkylation (preferably methylation) at the nitrogen atom or the alpha carbon of the amide bond linking two amino acids;
- modifications at the alpha carbon of the amide bond linking two amino acids such as e.g. acylation (preferably acetylation) or alkylation (preferably methylation) at the alpha carbon of the amide bond linking two amino acids.
- chirality changes such as e.g. replacement of one or more naturally occurring amino acids (L enantiomer) with the corresponding D-enantiomers;
- retro-inversions in which one or more naturally-occurring amino acids (L-enantiomer) are replaced with the corresponding D-enantiomers, together with an inversion of the amino acid chain (from the C-terminal end to the N-terminal end);
- azapeptides, in which one or more alpha carbons are replaced with nitrogen atoms; and/or
- betapeptides, in which the amino group of one or more amino acid is bonded to the β carbon rather than the a carbon.

The polypeptides comprising fragments of at least 6 consecutive amino acids of the PF4 muteins according to the invention and exhibiting an anti-angiogenic activity may further comprise sequences in addition to the conservative fragments of the PF4 muteins according to the invention. For example, they may comprise a signal peptide, a linker sequence or a second fragment of at least 6 consecutive amino acids of the PF4 muteins according to the invention.

In a specific embodiment, the polypeptides comprising fragments of at least 6 consecutive amino acids of the PF4 muteins according to the invention and exhibiting an anti-angiogenic activity consist of at least two non-consecutive fragments of at least 6 consecutive amino acids of the PF4 muteins according to the invention.

The PF4 muteins according to the invention and fragments thereof preferably exhibit an increased anti-angiogenic activity compared to the wild-type PF4 protein.

The PF4 muteins according to the invention and fragments thereof also preferably exhibit a decreased affinity for heparin and/or heparin sulfate compared to the wild-type PF4 protein. Methods for determining the affinity of a compound for heparin and/or heparin sulfate are well-known in the art. The affinity may for example be determining using surface plasmon resonance with a BIAcore equipment, as described in example 1.

In a preferred embodiment, the PF4 muteins according to the invention and fragments thereof exhibit at least one of the following characteristics:
  i. they have an affinity constant for heparin of at least 4, 8 or $10^3$ µM; and/or
  ii. they have an affinity constant for heparan sulfate of at least $10^2$, $3.10^2$ or $10^3$ µM; and/or
  iii. they have an $IC_{50}$, determined using the proliferation assay based on FGF-2 stimulated BAE, inferior to 160, 90 or 42 ng/ml.

The PF4 muteins according to the invention may for example exhibit characteristics (i) and (ii); (i) and (iii); (ii) and (iii); or (i), (ii) and (iii).

Therapeutic Use of PF4 Muteins and Fragments Thereof. The PF4 muteins according to the invention and fragments thereof exhibit an anti-angiogenic activity. Therefore, there are useful for inhibiting angiogenesis, both in vitro and in vivo.

Diseases in which is it desired to inhibit angiogenesis are well-known to the skilled in the art (see, e.g., Carmeliet 2005 Nature. 438:932-6). The disease may for example correspond to any one of the diseases listed in Supplementary table I of Carmeliet (2005 Nature. 438:932-6).

More specifically, the invention is directed to the PF4 muteins according to the invention and fragments thereof for use in the treatment of a disease selected from the group consisting of cancer, ocular neovascular disorders, inflammatory diseases, autoimmune diseases, infections, blood vessel diseases, skin diseases, lung diseases, intestine diseases, reproductive system diseases, bone and/or joint diseases, diabetes, obesity and cirrhosis.

As used herein, the term "cancer" refers to any type of malignant (i.e. non benign) tumor. The tumor preferably corresponds to a solid malignant tumor, which includes e.g.

carcinomas, adenocarcinomas, sarcomas, malignant melanomas, mesotheliomas and blastomas such as neuroblastomas, glioblastomas and retinoblastomas. Alternatively, the cancer may be a blood cancer such as a lymphoma or leukemia. The cancer may for example correspond to a lung, colorectal, pancreatic, stomach, laryngeal, nasopharyngeal, thyroid, bladder, penile, prostate, testicular, urethral, breast, cervical, endometrial, ovarian, vaginal, vulvar, liver, renal or retinal cancer. In a most preferred embodiment, the cancer is a metastatic cancer.

As used throughout the present specification, the term "ocular neovascular disorders" refers to disorders such as persistent hyperplastic vitreous syndrome, diabetic retinopathy (e.g. proliferative diabetic retinopathy), retinopathy of prematurity, ischemic retinopathy, intraocular neovascularization, age-related macular degeneration, corneal neovascularization, retinal neovascularization, choroidal neovascularization, diabetic macular edema, diabetic retina ischemia and diabetic retinal edema.

As used throughout the present specification, the term "inflammatory diseases" refers to a disease caused by or resulting in an inflammation. An inflammation is a pathologic process consisting of a dynamic complex of cytologic and chemical reactions that occur in the affected blood vessels and adjacent tissues in response to an injury or abnormal stimulation caused by a physical, chemical, or biologic agent. The inflammatory disease preferably corresponds to a chronic inflammatory disease.

As used throughout the present specification, the term "autoimmune disease" includes but is not limited to rheumatoid arthritis (RA), multiple sclerosis (MS), inflammatory bowel disease (IBD), Crohn's disease, systemic lupus erythematodes (SLE), Graves' disease and diabetes mellitus.

As used throughout the present specification, the term "infections" includes but is not limited to viral infections (e.g. AIDS) and bacterial infections.

As used throughout the present specification, the term "diabetes" includes both type I and type II diabetes.

By "blood vessel diseases" is meant diseases such as vascular malformations, DiGeorge syndrome, HHT, cavernous hemangioma, atherosclerosis and transplant arteriopathy.

By "skin diseases" is meant diseases such as psoriasis, warts, allergic dermatitis, scar keloids, pyogenic granulomas, blistering diseases and Kaposi sarcoma.

By "lung diseases" is meant diseases such as asthma, primary pulmonary hypertension and nasal polyps.

By "intestine diseases" is meant diseases such as inflammatory bowel disease, periodontal disease, ascites and peritoneal adhesions.

By "reproductive system diseases" is meant diseases such as endometriosis, uterine bleeding, ovarian cysts and ovarian hyperstimulation.

By "bone and/or joint diseases" is meant diseases such as arthritis, synovitis, osteomyelitis and osteophyte formation.

The invention is further directed to a method of inhibiting angiogenesis, and/or for treating or preventing a disease selected from the group consisting of cancer, ocular neovascular disorders, inflammatory diseases, autoimmune diseases, infections, blood vessel diseases, skin diseases, lung diseases, intestine diseases, reproductive system diseases, bone and/or joint diseases, diabetes, obesity and cirrhosis, comprising the step of administering an effective amount of a polypeptide as described herein to an individual in need thereof. Said individual in need thereof preferably suffers from or is at risk of suffering from a disease selected from the group consisting of cancer, ocular neovascular disorders, inflammatory diseases, autoimmune diseases, infections, blood vessel diseases, skin diseases, lung diseases, intestine diseases, reproductive system diseases, bone and/or joint diseases, diabetes, obesity and cirrhosis.

By "effective amount", is meant an amount sufficient to achieve a concentration of polypeptide which is capable of preventing, treating or slowing down the disease to be treated. Such concentrations can be routinely determined by those of skilled in the art. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like. It will also be appreciated by those of stalled in the art that the dosage may be dependent on the stability of the administered polypeptide.

By "treating" is meant a therapeutic use and by "preventing" is meant a prophylactic use.

The individuals to be treated in the frame of the invention are preferably human individuals. However, the veterinary use of the PF4 muteins according to the invention and fragments thereof for treating other mammals is also contemplated by the present invention.

The invention also pertains to use of nucleic acids encoding PF4 muteins according to the invention or fragments thereof, or vectors comprising such nucleic acids, for inhibiting angiogenesis.

Nucleic Acids, Host Cells and Methods for Producing Recombinant PF4 Muteins and Fragments Thereof.

An aspect of the invention pertains to a nucleic acid encoding a PF4 mutein according to the invention or a fragment thereof. The PF4 mutein or fragment thereof may correspond to any one of the polypeptides described in the above paragraph.

Such nucleic acids can easily be obtained by the skilled in the art by cloning the cDNA coding for wild-type PF4 and by introducing mutations by site-directed mutagenesis, e.g. as described in Example 1.

The nucleic acid may for example be comprised in a vector such as an expression vector. In such an expression vector, the nucleic acid according to the invention is placed under the control of signals (e.g. a promoter, a terminator and/or an enhancer) allowing the expression of the encoded polypeptide. The vector may further comprise a multiple cloning site, a selection marker, a detectable marker and the like.

The nucleic acids, optionally comprised in a vector, may then be introduced into a host cell. The invention thus pertains to a host cell comprising a nucleic acid according to the invention.

Such host cells are useful for producing recombinant muteins according to the invention or fragments thereof. Suitable host cells for the production of recombinant proteins are well-known in the art and include, e.g., bacterial cells (e.g. *E. coli*), yeast cells (e.g. *S. cerevisiae*), fungal cells (e.g. *A. niger*), plant cells, insect cells and mammalian cells such as CHO cells, mouse cells and human cells (e.g. HEK 293 and PER.C6).

The invention is thus directed to a method for producing a PF4 mutein according to the invention or fragments thereof comprising the steps of:
  a) providing the host cell according to the invention;
  b) cultivating said host cell under conditions suitable for producing said polypeptide; and, optionally,
  c) purifying said polypeptide, and optionally,
  d) formulating said polypeptide into a pharmaceutical composition.

Alternatively, the PF4 mutein according to the invention or fragments thereof may be produced chemical synthesis. Indeed, chemical synthesis is especially adapted for producing small peptides.

Pharmaceutical Compositions Comprising PF4 Muteins and/or Fragments Thereof.

The PF4 mutein according to the invention or fragments thereof may be formulated into a pharmaceutical composition. Thus the invention contemplates a pharmaceutical composition comprising a PF4 mutein according to the invention or fragments thereof and a physiologically acceptable carrier. Physiologically acceptable carriers can be prepared by any method known by those skilled in the art.

Pharmaceutical compositions comprising a PF4 mutein according to the invention or fragments thereof include all compositions wherein the polypeptide(s) and/or peptide(s) are contained in an amount effective to achieve the intended purpose. In addition, the pharmaceutical compositions may contain suitable pharmaceutically acceptable carriers comprising excipients and auxiliaries which facilitate processing of the active compounds into preparations which can be used pharmaceutically. Suitable pharmaceutically acceptable vehicles are well known in the art and are described for example in Remington's Pharmaceutical Sciences (Mack Publishing Company, Easton, USA, 1985), which is a standard reference text in this field. Pharmaceutically acceptable vehicles can be routinely selected in accordance with the mode of administration, solubility and stability of the peptides. For example, formulations for intravenous administration may include sterile aqueous solutions which may also contain buffers, diluents and other suitable additives. The use of biomaterials and other polymers for drug delivery, as well the different techniques and models to validate a specific mode of administration, are disclosed in literature.

The PF4 mutein according to the invention or fragments thereof may be administered by any means that achieve the intended purpose. For example, administration may be achieved by a number of different routes including, but not limited to subcutaneous, intravenous, intradermal, intramuscular, intraperitoneal, intracerebral, intrathecal, intranasal, oral, rectal, transdermal, buccal, topical, local, inhalant or subcutaneous use.

Dosages to be administered depend on individual needs, on the desired effect and the chosen route of administration. It is understood that the dosage administered will be dependent upon the age, sex, health, and weight of the recipient, concurrent treatment, if any, frequency of treatment, and the nature of the effect desired. The total dose required for each treatment may be administered by multiple doses or in a single dose.

Depending on the intended route of delivery, the compounds may be formulated as liquid (e.g., solutions, suspensions), solid (e.g., pills, tablets, suppositories) or semisolid (e.g., creams, gels) forms.

In a preferred embodiment, the compositions are presented in unit dosage forms to facilitate accurate dosing. The term "unit dosage forms" refers to physically discrete units suitable as unitary dosages for human subjects and other mammals, each unit containing a pre-determined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

The PF4 mutein according to the invention or fragments thereof can also be administered in sustained release forms or from sustained release drug delivery systems.

The expression "physiologically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Besides the pharmaceutically acceptable carrier, the compositions of the invention can also comprise minor amounts of additives, such as stabilizers, excipients, buffers and preservatives.

The invention also contemplates a pharmaceutical composition comprising a nucleic acid encoding a PF4 mutein according to the invention or fragments thereof in the frame of e.g. a treatment by gene therapy. In this case, the nucleic acid is preferably present on a vector, on which the sequence coding for the peptide is placed under the control of expression signals (e.g. a promoter, a terminator and/or an enhancer) allowing its expression. The vector may for example correspond to a viral vector such as an adenoviral or a lentiviral vector.

The invention further provides kits comprising a pharmaceutical composition comprising a PF4 mutein according to the invention or fragments thereof and instructions regarding the mode of administration. These instructions may e.g. indicate the medical indication, and/or the route of administration, and/or the dosage, and/or the group of patients to be treated.

All references cited herein, including journal articles or abstracts, published or unpublished patent application, issued patents or any other references, are entirely incorporated by reference herein, including all data, tables, figures and text presented in the cited references.

Although having distinct meanings, the terms "comprising", "having", "containing' and "consisting of" have been used interchangeably throughout this specification and may be replaced with one another.

The invention will be further evaluated in view of the following examples and figures.

FIG. 2 shows that the mutation histidine 67 is critical for modulate the biological activity of the chemokine PF4. Different concentrations of recombinant proteins were added in the proliferation assay using FGF-2 stimulated bovine aortic endothelial cells (BAEC). Results are the means±s.e.m. of three independent experiments realized in triplicate.

BRIEF DESCRIPTION OF THE SEQUENCES

SEQ ID NO: 1 shows the sequence of the full-length wild-type PF4 protein.

SEQ ID NO: 2 shows the sequence of the mature wild-type PF4 protein.

SEQ ID NO: 3 shows the sequence of the PF4-241 mutant.

SEQ ID NO: 4 shows the sequence of a PF4 mutein comprising a L67H mutation.

SEQ ID NO: 5 shows the sequence of a PF4 mutein comprising a P58L mutation and a L67H mutation.

SEQ ID NO: 6 shows the sequence of a PF4-241 mutant comprising a L67H mutation.

SEQ ID NO: 7 shows the sequence of a PF4 mutein comprising a Q56R mutation and a L67H mutation.

SEQ ID NO: 8 shows the sequence of a PF4-241 mutant comprising a Q56R mutation and a L67H mutation.

SEQ ID NO: 9 shows the sequence of a peptide according to the invention comprising a Q56R mutation and a L67H mutation.

EXAMPLES

Example 1

Material and Methods 1.1. Cell Culture

BAE cells were grown in DMEM (Invitrogen, Cergy Pontoise, France) containing antibiotics, 1% glutamine, and 10% fetal calf serum or 10% calf serum and were maintained in a 37° C. and 10% $CO_2$.

1.2. Plasmids

The coding region of human PF4/CXCL4 cDNA was cloned from pCDNA-PF4 in two consecutive steps. First, a rather long PF4 cDNA fragment was amplified by primers binding PF4.

The amplicon (306 bp) was cloned into the pSC-A vector (Stratagene). The reconstructed plasmid was verified by DNA sequencing. This construct was used as a template to amplify the coding region of the mature PF4 protein. The purified PCR product was digested with BamH1 and Xho1 restriction enzymes and inserted into the plasmid pGEX-6P-2 (Amersham Biosciences) to generate the pGEX-PF4 expression vector. Finally, automated DNA Sequencing Analysis checked the nucleotide sequence of the selected clones.

1.3. Construction of Recombinants pGEX-PF4 Mutants Expression Vectors

The pGEX-PF4 expression vector was used as the DNA template for site-directed mutagenesis procedure using QuikChange II XL kit (Stratagen). Finally, screening of pGEX-PF4 mutants clones were performed by DNA sequencing analysis as described earlier (Lasagni et al. 2007 Blood. 2007 109:4127-34; Bastide et al. 2008 Nucleic Acids Res. 36:2434-45).

1.4. Production of Recombinants PF4 and Mutants in *E. coli*

*E. coli* BL21 (DE3) transformed with the pGEX-6P-2 (GST-fusion expression vector, Amersham) recombinant vector containing the different CDNAs described before, were grown in 100 ml LB with 100 µg/ml ampicillin. After the $OD_{600nm}$ reached 0.3-0.5, the expression of the fusion protein was induced by the addition with shaking of 0.5 mmol/L isopropyl-1-thio-β-D-galactopyranoside (IPTG) (Euromedex). Cultures were grown overnight at 220 rpm and 25° C. The IPTG-induced test cultures and the IPTG-induced control culture containing the empty vector pGEX-6P-2 were collected by centrifugation at 5000 r/min for 15 minutes at 4° C. The pellets were resuspended in 10 volumes of lysis buffer containing PBS 1× (10 mM $Na_2HPO_4$, 1.8 mM $KH_2PO_4$, 140 mM NaCl, 2.7 mM KCl, pH 7.3, Lonza), 1 mg/ml lysozyme (Sigma) and cocktail inhibitor protease (Roche). Cells were lyzed by freeze/thaw, using liquid nitrogen, followed by sonication (six 30-s sonication steps) in an ice bath. For complete fragmentation of DNA, 5 g/ml DNase I (Sigma) was added and stirred on ice for 15 min. The cell debris was removed by centrifugation at 12 000 r/min for 30 minutes at 4° C. and the supernatant was collected.

1.5. Affinity Chromatography Step for GST-PF4 and Mutants Recombinant Proteins Purification The supernatant containing the soluble GST-PF4 (or an another variant) recombinant protein was loaded on a GSTrap HP affinity column (5 ml; Amersham Biosciences) pre-equilibrated with PBS IX at a flow rate of 1 ml/min at room temperature. The bound material was washed with PBS IX until the absorbance at an OD of 280 nm returned to baseline. Once the baseline was stable, elution of the bound GST-PF4 recombinant protein was carried out using ten column volumes of elution buffer (PBS IX, 20 mM reduced glutathione, pH 8.0) at a 1 ml/min flow rate. The eluted fractions containing the GST-PF4 recombinant protein were pooled. The purification stages and affinity chromatographic profiles were analyzed by Coomassie Blue-stained (Biorad) SDS-PAGE gels and by western blot analysis.

1.6. Cell Viability Assay

BAE cells were plated for 24 h in flat-bottomed 96-well plates at $5 \times 10^3$ cells/well. Following overnight serum starvation, cells were treated in triplicate for 48 h with 10 ng/ml of recombinant FGF2 and in the presence or absence of different concentrations of recombinants proteins. Cell viability was measured at 490 nm using the CellTiter 96 $AQ_{ueous}$ One Solution cell proliferation assay (Promega) following the manufacturer's instructions.

1.7. SPR (Surface Plasmon Resonance)

Real-time binding experiments were performed with a BIAcore 3000 biosensor instrument (BIAcore AB) and quantified in terms of resonance units (RU) (1000 RU=1 ng of protein bound/$mm^2$ of flow cell surface) (Ferjoux et al. 2003 Mol Biol Cell. 14:3911-28). Glyco Amino Glycans (GAGs) were biotinylated and immobilized on a carboxymethylated dextran chip pre-immobilized with streptavidin (chip SA, BIAcore AB). Heparin (140 RU) and Heparane Sufate (120RU) were immobilized on flow cell 2 and flow cell 3, whereas flow cell 1 was used as a nonspecific interaction reference. Soluble ligands were injected at a flow rate of 30 µl/min, exposed to the surface for 600 s (association phase) followed by a 300 s flow running during which the dissociation occurred. Sensorgrams are representative of specific interactions (differential response) where non-specific binding that occurred on flow cell 1 was deduced from binding that occurred on flow cell 2 and 3.

Results are expressed as resonance units (RU) as a function of time in seconds. A kinetic analysis to determine association, dissociation, and affinity constants (ka, kd, and KD, respectively) was carried out for all recombinants proteins by injecting different concentrations (16-2000 nM) of proteins over immobilized GAGs. The analysis was carried out by fitting the overlaid sensorgrams with the 1:1 Languimuir binding model with mass transfer of the BIAevaluation 3.1 software. The dissociation rate of the complexes of recombinants proteins with GAGs were not influenced by the contact time (from 4 up to 8 min).

1.8. ELISA

PF4 and variants were measured using the commercial PF4-ELISA kits (R&D Systems). PBS was used as blank.

Assays were performed in triplicate and results analyzed using the Softmax Pro4.0 software (Molecular Devices).

Example 2

Results

The following proteins were produced as recombinant proteins in *E. coli*:

the wild-type PF4 protein (referred to as "PF4", SEQ ID NO: 2);

the PF4 P58L mutant (referred to as "L", SEQ ID NO: 2 in which the proline at position 58 is substituted for a leucine);

the PF4 K66E mutant (referred to as "E", SEQ ID NO: 2 in which the lysine at position 66 is substituted for a glutamic acid);

the PF4 P58L K66E mutant (referred to as "LE", SEQ ID NO: 2 in which the proline at position 58 is substituted for a leucine and the lysine at position 66 is substituted for a glutamic acid);

the PF4 P58L L67H mutein (referred to as "LH", SEQ ID NO: 2 in which the proline at position 58 is substituted for a leucine and the leucine at position 67 is substituted for a histidine);

the PF4 K66E L67H mutein (referred to as "EH", SEQ ID NO: 2 in which the lysine at position 66 is substituted for a glutamic acid and the leucine at position 67 is substituted for a histidine);

the PF4-241 mutant (referred to as "241", SEQ ID NO: 6); and the PF4-241 L67H mutein (referred to as "241+H", SEQ ID NO: 6 in which the leucine at position 67 is substituted for a histidine).

Correct expression of the different proteins was verified by Coomassie staining and by anti-PF4 Western Blot.

Figure 1:
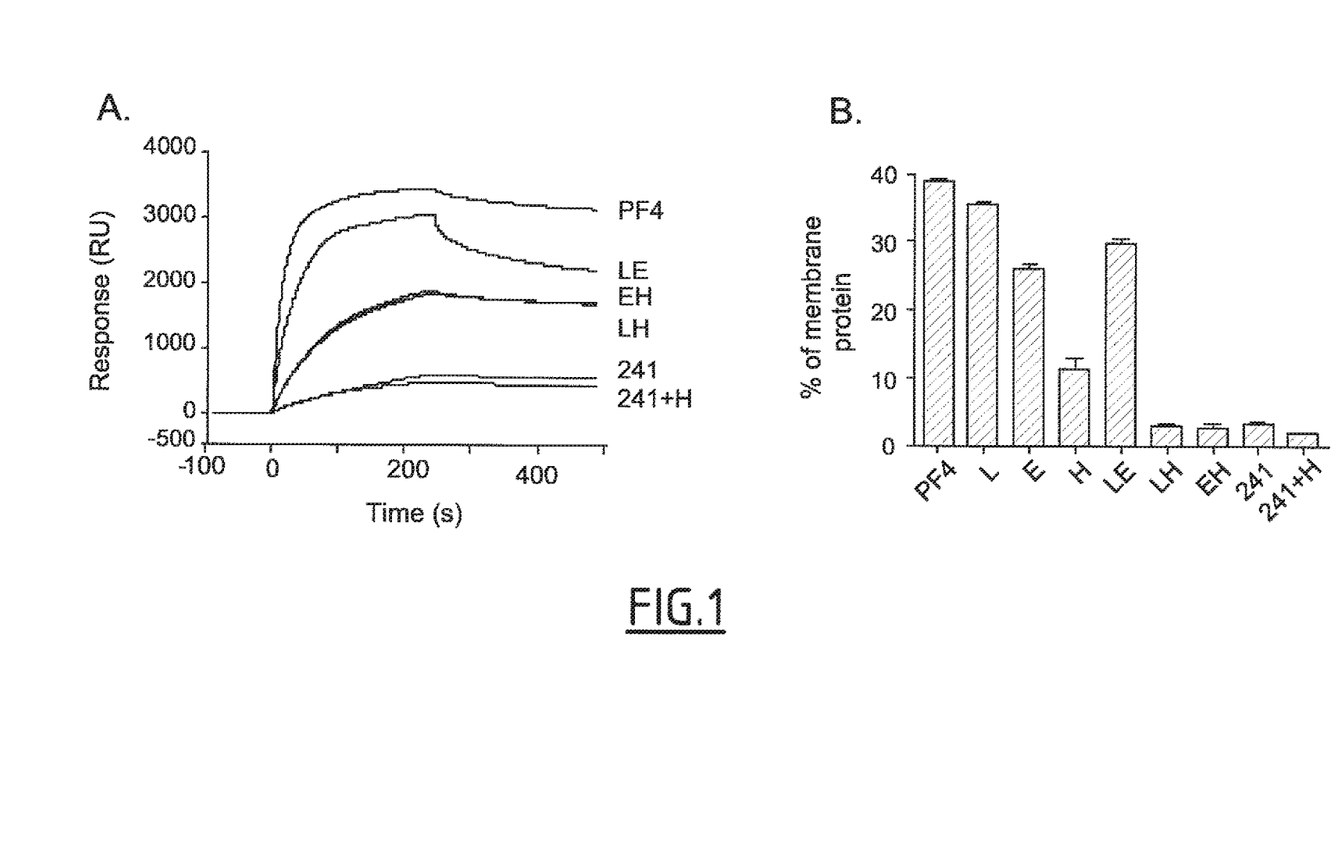
FIG. 1 shows that the mutation of histidine 67 is critical for modulating the GAGs affinities of the chemokine PF4. A. Biacore analysis, 2 uM of the different proteins are injected over immobilized heparin and heparan sulfate. B. Ex vivo PF4 and mutants diffusibility. The amount of protein associated membrane was determinated by specific anti-PF4 ELISA. Results are the means±s.e.m. of three independent experiments realized in triplicate.

The binding of the different proteins to heparin and heparin sulfate was analyzed by Biacore and the diffusibility was analyzed by ELISA. The results are shown on FIG. 1. It was found that muteins comprising the L67H mutation exhibit a better diffusibility than proteins lacking the L67H mutation. The diffusibility was even higher when the L67H mutation was associated with the K61Q, the K62E, the K65Q and the K66E mutations (see 241+H).

The affinity constant of the different proteins for immobilized heparin and heparan sulphate, as determined by Biacore binding studies, is shown in Table 1 below. When the L67H mutation is present, the affinity of the mutein for heparin drops by 3 logs, and that to heparan sulfate by 5 logs.

TABLE 1

|  | KD (μM) | |
| --- | --- | --- |
|  | Heparin | Heparan sulfate |
| PF4 | $1.59 \, 10^{-3}$ | $8.5 \, 10^{-3}$ |
| PF4 P58L (L) | $2.63 \, 10^{-3}$ | $5.25 \, 10^{-2}$ |
| PF4 K66E (E) | $1.44 \, 10^{-3}$ | $1.02 \, 10^{-2}$ |
| PF4 P58L K66E (LE) | $3.34 \, 10^{-3}$ | $3.29 \, 10^{-2}$ |
| PF4 P58L L67H (LH) | 8.61 | $1.15 \, 10^2$ |
| PF4 K66E L67H (EH) | 4.21 | $3.83 \, 10^2$ |
| PF4 241 (241) | $>10^3$ | $>10^3$ |
| PF4 241 L67H (241+H) | $>10^3$ | $>10^3$ |

Figure 2A:
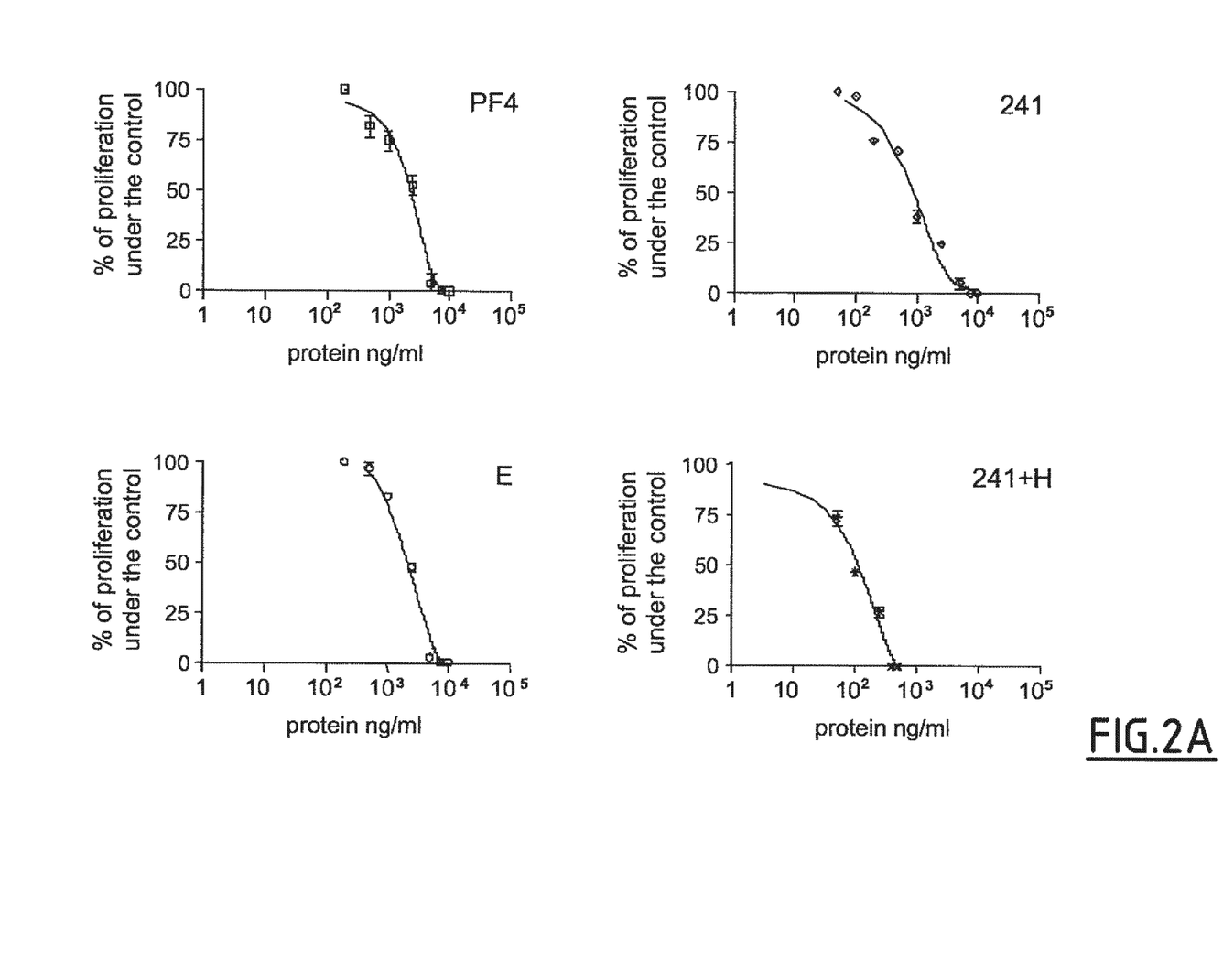
Figure 2B:
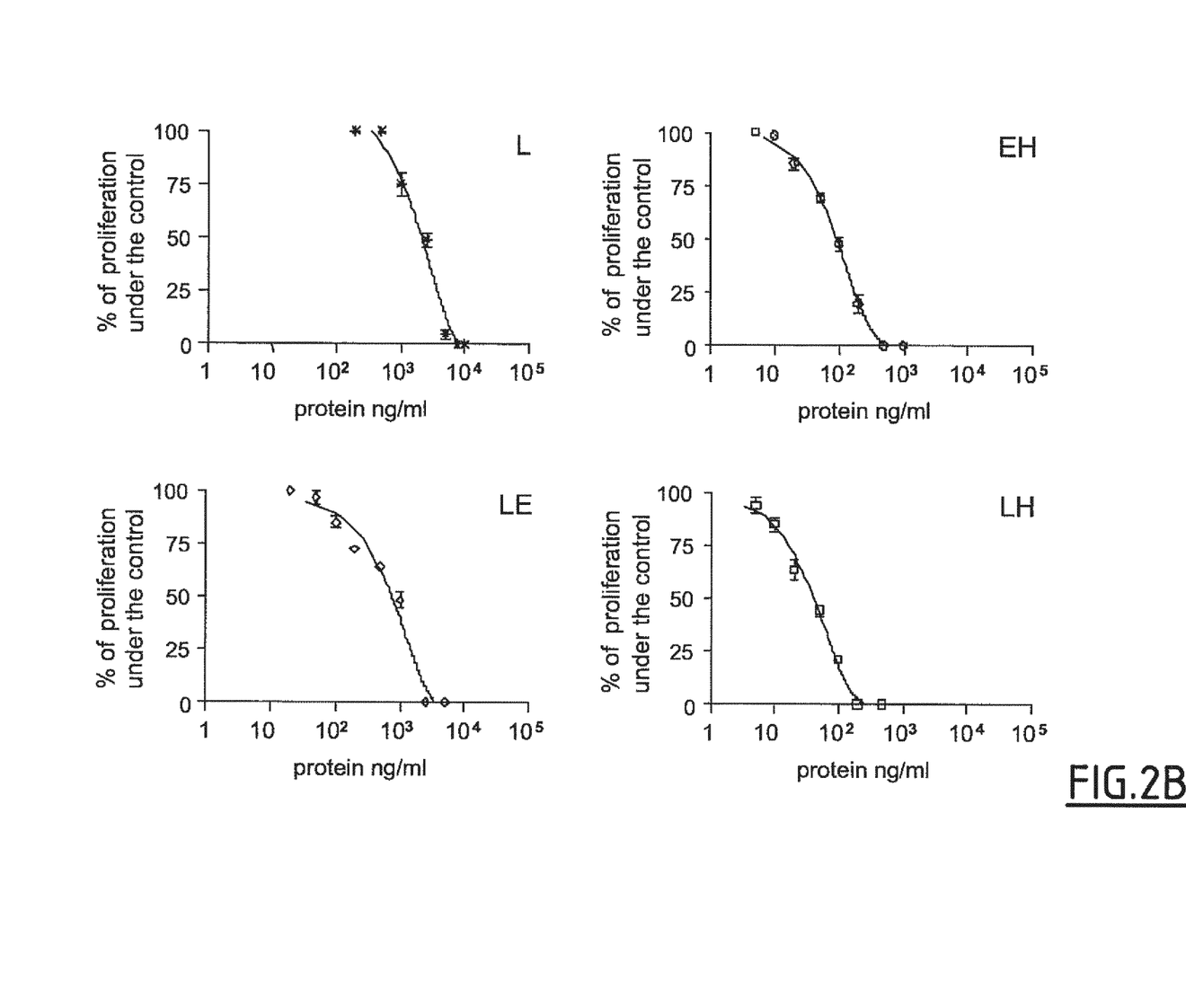

The anti-angiogenic activity of the different proteins was studied using the proliferation assay based on FGF-2 stimulated bovine aortic endothelial cells (BAEC). The dose-response curves are shown on FIG. 2. These curves allowed calculating the half maximal inhibitory concentration ($IC_{50}$) of the different proteins, as shown in Table 2. The 1050 values when calculated in molar units (MW as tetrameric form of 28 kDa) are of 1 nM for the L67H mutants, while it is of 84 nM for the wild-type PF4 protein.

TABLE 2

|  | ng/ml | |
| --- | --- | --- |
|  | IC50 | Imax |
| PF4 | $2.26 \, 10^3$ | $5 \, 10^3$ |
| PF4 P58L (L) | $1.99 \, 10^3$ | $5 \, 10^3$ |
| PF4 K66E (E) | $2.03 \, 10^3$ | $5 \, 10^3$ |
| PF4 P58L K66E (LE) | 854 | $2.5 \, 10^3$ |
| PF4 P58L L67H (LH) | 41.56 | 200 |
| PF4 K66E L67H (EH) | 89.16 | 250 |
| PF4 241 (241) | 839.1 | $5 \, 10^3$ |
| PF4 241 L67H (241+H) | 150 | 400 |

In conclusion, it was found that the L67H mutation is critical for modulating the biological activity of PF4.

The invention claimed is:

1. A polypeptide selected from the group consisting of SEQ ID Nos.: 4, 5, 6, 7, or 8, or a fragment of at least 10 consecutive amino acids of said polypeptide, wherein said fragment includes positions 58 to 67 of SEQ ID NO:2.

2. The polypeptide according to claim 1, wherein the leucine at position 67 of SEQ ID NO: 2 is replaced with histidine.

3. The polypeptide according to claim 1, wherein said polypeptide differs from the sequence of SEQ ID NO: 2 or 3 only by the presence of one or two amino acid substitutions.

4. The polypeptide according to claim 1, wherein said polypeptide comprises the sequence of any one of SEQ ID NOs: 4, 5, 6, 7 or 8.

5. A fragment according to claim 1, wherein said fragment includes positions 58 to 67 of SEQ ID NO: 2.

6. The polypeptide or fragment thereof according claim 1, wherein said polypeptide or fragment thereof exhibits an increased anti-angiogenic activity and a decreased affinity for heparin and/or heparin sulfate compared to the wild-type PF4 protein of SEQ ID NO: 2.

7. A nucleic acid that encodes a polypeptide or a fragment as set forth in claim 1.

8. A host cell comprising a nucleic acid as set forth in claim 7.

9. A pharmaceutical composition that comprises a polypeptide or a fragment as set forth in claim 1.

10. A method for producing a polypeptide or a fragment of claim 1, comprising the steps of:
  a) providing a host cell of claim 8;
  b) cultivating said host cell under conditions suitable for producing said polypeptide or said fragment; and, optionally,
  c) purifiying said polypeptide or said fragment, and optionally,
  d) formulating said polypeptide or said fragment into a pharmaceutical composition.

11. A method of inhibiting angiogenesis in vivo in a patient in need thereof, comprising the step of
  administering to said patient a polypeptide or a fragment as set forth in claim 1.

12. A method of treating ocular neovascular disorder, comprising
  administering to a patient with said ocular neovascular disorder a polypeptide or a fragment as set forth in claim 1.

13. A polypeptide comprising a fragment according to claim 1, said polypeptide exhibiting an anti-angiogenic activity.

14. The polypeptide according to claim 13, wherein said polypeptide comprises a sequence identical to amino acids 60 to 67 of any one of sequences SEQ ID NO: 4, 5or 6.

15. The polypeptide according to claim 13, wherein said polypeptide comprises at least 10 consecutive amino acids of any one of sequences SEQ ID NO: 4, 5, 6, 7 or 8.

* * * * *

SEQUENCE LISTING

```
<160> NUMBER OF SEQ ID NOS: 9

<210> SEQ ID NO 1
<211> LENGTH: 101
<212> TYPE: PRT
<213> ORGANISM: Homo sapiens
<220> FEATURE:
<221> NAME/KEY: SIGNAL
<222> LOCATION: (1)..(31)
<220> FEATURE:
<221> NAME/KEY: CHAIN
<222> LOCATION: (32)..(101)
<223> OTHER INFORMATION: Platelet factor 4
<220> FEATURE:
<221> NAME/KEY: CHAIN
<222> LOCATION: (48)..(101)
<223> OTHER INFORMATION: Platelet factor 4, short form

<400> SEQUENCE: 1

Met Ser Ser Ala Ala Gly Phe Cys Ala Ser Arg Pro Gly Leu Leu Phe
1               5                   10                  15
```

Leu Gly Leu Leu Leu Leu Pro Leu Val Val Ala Phe Ala Ser Ala Glu
            20                  25                  30

Ala Glu Glu Asp Gly Asp Leu Gln Cys Leu Cys Val Lys Thr Thr Ser
        35                  40                  45

Gln Val Arg Pro Arg His Ile Thr Ser Leu Glu Val Ile Lys Ala Gly
50                  55                  60

Pro His Cys Pro Thr Ala Gln Leu Ile Ala Thr Leu Lys Asn Gly Arg
65                  70                  75                  80

Lys Ile Cys Leu Asp Leu Gln Ala Pro Leu Tyr Lys Lys Ile Ile Lys
                85                  90                  95

Lys Leu Leu Glu Ser
            100

<210> SEQ ID NO 2
<211> LENGTH: 70
<212> TYPE: PRT
<213> ORGANISM: Homo sapiens

<400> SEQUENCE: 2

Glu Ala Glu Glu Asp Gly Asp Leu Gln Cys Leu Cys Val Lys Thr Thr
1               5                  10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
50                  55                  60

Lys Lys Leu Leu Glu Ser
65                  70

<210> SEQ ID NO 3
<211> LENGTH: 70
<212> TYPE: PRT
<213> ORGANISM: Artificial
<220> FEATURE:
<223> OTHER INFORMATION: Synthetic PF4 mutant protein
<220> FEATURE:
<221> NAME/KEY: MISC_FEATURE
<222> LOCATION: (61)..(61)
<223> OTHER INFORMATION: K61Q mutation
<220> FEATURE:
<221> NAME/KEY: MISC_FEATURE
<222> LOCATION: (62)..(62)
<223> OTHER INFORMATION: K62E mutation
<220> FEATURE:
<221> NAME/KEY: MISC_FEATURE
<222> LOCATION: (65)..(65)
<223> OTHER INFORMATION: K65Q mutation
<220> FEATURE:
<221> NAME/KEY: MISC_FEATURE
<222> LOCATION: (66)..(66)
<223> OTHER INFORMATION: K66E mutation

<400> SEQUENCE: 3

Glu Ala Glu Glu Asp Gly Asp Leu Gln Cys Leu Cys Val Lys Thr Thr
1               5                  10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Gln Glu Ile Ile
50                  55                  60

```
Gln Glu Leu Leu Glu Ser
 65                 70

<210> SEQ ID NO 4
<211> LENGTH: 70
<212> TYPE: PRT
<213> ORGANISM: Artificial
<220> FEATURE:
<223> OTHER INFORMATION: Synthetic PF4 mutant protein
<220> FEATURE:
<221> NAME/KEY: MISC_FEATURE
<222> LOCATION: (67)..(67)
<223> OTHER INFORMATION: L67H mutation

<400> SEQUENCE: 4

Glu Ala Glu Glu Asp Gly Asp Leu Gln Cys Leu Cys Val Lys Thr Thr
 1               5                  10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys His Leu Glu Ser
 65                 70

<210> SEQ ID NO 5
<211> LENGTH: 70
<212> TYPE: PRT
<213> ORGANISM: Artificial
<220> FEATURE:
<223> OTHER INFORMATION: Synthetic PF4 mutant protein
<220> FEATURE:
<221> NAME/KEY: MISC_FEATURE
<222> LOCATION: (58)..(58)
<223> OTHER INFORMATION: P58L mutation
<220> FEATURE:
<221> NAME/KEY: MISC_FEATURE
<222> LOCATION: (67)..(67)
<223> OTHER INFORMATION: L67H mutation

<400> SEQUENCE: 5

Glu Ala Glu Glu Asp Gly Asp Leu Gln Cys Leu Cys Val Lys Thr Thr
 1               5                  10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Leu Leu Tyr Lys Lys Ile Ile
    50                  55                  60

Lys Lys His Leu Glu Ser
 65                 70

<210> SEQ ID NO 6
<211> LENGTH: 70
<212> TYPE: PRT
<213> ORGANISM: Artificial
<220> FEATURE:
<223> OTHER INFORMATION: Synthetic PF4 mutant protein
<220> FEATURE:
<221> NAME/KEY: MISC_FEATURE
<222> LOCATION: (61)..(61)
<223> OTHER INFORMATION: K61Q mutation
<220> FEATURE:
<221> NAME/KEY: MISC_FEATURE
```

```
<222> LOCATION: (62)..(62)
<223> OTHER INFORMATION: K62E mutation
<220> FEATURE:
<221> NAME/KEY: MISC_FEATURE
<222> LOCATION: (65)..(65)
<223> OTHER INFORMATION: K65Q mutation
<220> FEATURE:
<221> NAME/KEY: MISC_FEATURE
<222> LOCATION: (66)..(66)
<223> OTHER INFORMATION: K66E mutation
<220> FEATURE:
<221> NAME/KEY: MISC_FEATURE
<222> LOCATION: (67)..(67)
<223> OTHER INFORMATION: L67H mutation

<400> SEQUENCE: 6

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Gln Glu Ile Ile
    50                  55                  60

Gln Glu His Leu Glu Ser
65                  70

<210> SEQ ID NO 7
<211> LENGTH: 70
<212> TYPE: PRT
<213> ORGANISM: Artificial
<220> FEATURE:
<223> OTHER INFORMATION: Synthetic PF4 mutant protein
<220> FEATURE:
<221> NAME/KEY: MISC_FEATURE
<222> LOCATION: (56)..(56)
<223> OTHER INFORMATION: Q56R mutation
<220> FEATURE:
<221> NAME/KEY: MISC_FEATURE
<222> LOCATION: (67)..(67)
<223> OTHER INFORMATION: L67H mutation

<400> SEQUENCE: 7

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Arg Ala Pro Leu Tyr Lys Lys Ile Ile
    50                  55                  60

Lys Lys His Leu Glu Ser
65                  70

<210> SEQ ID NO 8
<211> LENGTH: 70
<212> TYPE: PRT
<213> ORGANISM: Artificial
<220> FEATURE:
<223> OTHER INFORMATION: Synthetic PF4 mutant protein
<220> FEATURE:
<221> NAME/KEY: MISC_FEATURE
<222> LOCATION: (56)..(56)
<223> OTHER INFORMATION: Q56R mutation
<220> FEATURE:
<221> NAME/KEY: MISC_FEATURE
<222> LOCATION: (61)..(61)
```

```
<223> OTHER INFORMATION: K61Q mutation
<220> FEATURE:
<221> NAME/KEY: MISC_FEATURE
<222> LOCATION: (62)..(62)
<223> OTHER INFORMATION: K62E mutation
<220> FEATURE:
<221> NAME/KEY: MISC_FEATURE
<222> LOCATION: (65)..(65)
<223> OTHER INFORMATION: K65Q mutation
<220> FEATURE:
<221> NAME/KEY: MISC_FEATURE
<222> LOCATION: (66)..(66)
<223> OTHER INFORMATION: K66E mutation
<220> FEATURE:
<221> NAME/KEY: MISC_FEATURE
<222> LOCATION: (67)..(67)
<223> OTHER INFORMATION: L67H mutation

<400> SEQUENCE: 8

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Arg Ala Pro Leu Tyr Gln Glu Ile Ile
    50                  55                  60

Gln Glu His Leu Glu Ser
65                  70

<210> SEQ ID NO 9
<211> LENGTH: 42
<212> TYPE: PRT
<213> ORGANISM: Artificial
<220> FEATURE:
<223> OTHER INFORMATION: Synthetic PF4 mutant peptide
<220> FEATURE:
<221> NAME/KEY: MISC_FEATURE
<222> LOCATION: (28)..(28)
<223> OTHER INFORMATION: Q56R mutation
<220> FEATURE:
<221> NAME/KEY: MISC_FEATURE
<222> LOCATION: (39)..(39)
<223> OTHER INFORMATION: L67H mutation

<400> SEQUENCE: 9

Ser Gln Val Arg Pro Arg His Ile Thr Ser Leu Glu Val Ile Lys Ala
1               5                   10                  15

Gly Pro Asn Gly Arg Lys Ile Cys Leu Asp Leu Arg Ala Pro Leu Tyr
            20                  25                  30

Lys Lys Ile Ile Lys Lys His Leu Glu Ser
        35                  40
```